United States Patent
Hameister et al.

(10) Patent No.: US 6,427,057 B1
(45) Date of Patent: Jul. 30, 2002

(54) IMAGE-FORMING MACHINE WITH A PULSE DENSITOMETER

(75) Inventors: William A. Hameister, Penfield; Kenneth P. Friedrich, Honeoye, both of NY (US)

(73) Assignee: Heidelberger Druckmaschinen AG, Heidelberg (DE)

( * ) Notice: Subject to any disclaimer, the term of this patent is extended or adjusted under 35 U.S.C. 154(b) by 0 days.

(21) Appl. No.: 09/737,320

(22) Filed: Dec. 14, 2000

(51) Int. Cl.[7] ............................................. G03G 15/00
(52) U.S. Cl. ...................................................... 399/74
(58) Field of Search ............................. 399/26, 31, 49, 399/72, 74, 78, 64, 160, 196; 250/338.1, 559.02, 559.1, 559.99; 356/432, 434, 443, 445; 378/101, 108; 396/563

(56) References Cited

U.S. PATENT DOCUMENTS

| | | | |
|---|---|---|---|
| 3,756,725 A | 9/1973 | Manring | 356/425 |
| 3,876,106 A | * 4/1975 | Powell et al. | 399/64 |
| 4,003,600 A | 1/1977 | Christie, Jr. et al. | 297/452.54 |
| 4,047,819 A | 9/1977 | Goldberg | 356/434 |
| 4,194,838 A | 3/1980 | Bey et al. | 356/404 |
| 4,229,107 A | 10/1980 | Childers | 356/443 |
| 4,236,826 A | 12/1980 | Yamanishi | 356/432 |
| 4,473,029 A | 9/1984 | Fritz et al. | 399/236 |
| 4,546,060 A | 10/1985 | Miskinis et al. | 430/111.31 |
| 4,550,254 A | 10/1985 | Zomorrodi et al. | 250/338.1 |
| 4,673,807 A | 6/1987 | Kobayashi et al. | 250/214 AG |
| 4,974,022 A | * 11/1990 | Nezu | 399/196 |
| 5,117,119 A | 5/1992 | Schubert et al. | 250/559.02 |
| 5,119,132 A | 6/1992 | Butler | 399/49 |
| 5,173,750 A | 12/1992 | Laukaitis | 356/445 |
| 5,319,696 A | 6/1994 | Abdel-Malek et al. | 378/108 |
| 5,519,497 A | 5/1996 | Hubble, III et al. | 356/445 |
| 5,649,266 A | 7/1997 | Rushing | 399/59 |
| 5,966,573 A | * 10/1999 | Yu et al. | 399/160 |
| 6,229,972 B1 | * 5/2001 | Rushing | 399/74 |

OTHER PUBLICATIONS

Allen J. Rushing, Ph.D., Letter dated Oct. 23, 2000, 2 pages.

* cited by examiner

*Primary Examiner*—Sophia S. Chen
*Assistant Examiner*—Hoan Tran

(57) ABSTRACT

This invention provides an image-forming machine with a pulse densitometer that avoids the formation of artifacts on electrophotographic films. The image-forming machine may have a charger, an exposure machine, a toning station, a transfer charger, a fusing station, and a densitometer positioned next to a photoconductor. The densitometer may have an emitter, a collector, and a pulse apparatus. The densitometer provides one or more pulses to measure the toner and photoconductor densities. The pulsed emissions are essentially below the exposure threshold of electrophotographic films, especially those sensitive to the infrared spectral region.

49 Claims, 3 Drawing Sheets

IMAGE-FORMING MACHINE WITH A PULSE DENSITOMETER

This application is based on Provisional Application No. 60/225, 486 having the title "An Image-Formning Machine with a Pulse Densitometer" filed on Aug. 15, 2000. The benefit of the filing date of the Provisional Application is claimed for in this application.

FIELD OF THE INVENTION

This invention relates generally to image-forming machines with densitometers. More particularly, this invention relates to electrophotographic image-forming machines with on-line densitometers.

BACKGROUND OF THE INVENTION

Electrophotographic (EP) image-forming machines are used to transfer images onto paper or other medium. An EP image-forming machine usually has a photoconductor with a film, which is electrostatically charged and optically exposed to form an electrostatic latent image on the surface. Toner is deposited onto the photoconductor. The toner is charged, thus adhering to the photoconductor surface in areas corresponding to the electrostatic latent image. The toner image is transferred to the paper or other medium. The paper is heated for the toner to fuse to the paper. The photoconductor is then refreshed—cleaned to remove any residual toner and charge—making it ready for another image.

Many EP image-forming machines have a densitometer to assist with operating and controlling the image-forming process. The densitometer determines the density of the toner on the photoconductor, from which operating adjustments are made. The densitometer typically is a transmission densitometer, which has an emitter and a collector on opposite sides of the photoconductor. The emitter may be made of a GaAIAs chip having a wavelength of about 880 nm. The optical path passing between the emitter and collector also passes through the photoconductor and any toner on it. The densitometer provides a voltage reading corresponding to the amount of light energy passing from the emitter to the collector. The voltage reading also corresponds to the density of the photoconductor and any toner on it.

The densitometer usually works in conjunction with a process patch, which is on the surface of the photoconductor in an interframe or edge area. As the EP image-forming machine operates, the process patch is charged, exposed, and developed to provide the maximum toner density on the process patch. The densitometer provides the density at the process patch and at a place on the photoconductor without toner—adjacent to the process patch and outside the image frames. The voltage reading of the photoconductor without toner is subtracted from the voltage reading of the process patch (photoconductor and toner) to provide the density of toner on the photoconductor process patch.

Photoconductors typically have three layers—a support underlayer made of polyester or similar material, a center conductive layer, and an electrographic surface or film. Older film designs are optically and electrostatically sensitive, but are essentially not sensitive to the infrared spectral region. The emitter and collector typically operate in the infrared range; thus making these older films relatively impervious to the emissions of the densitometer. While these films may experience some effect from the densitometer, these effects are relatively unnoticeable in the output image.

Recent film designs are sensitive to densitometers in current use. Newer films are sensitive to the infrared spectral region. Since densitometers are responsive to infrared emissions, the emitters may cause artifacts—unwanted images—to appear on the newer films and, consequently, the output images from the machine. The types of artifacts vary. However, densitometers generally make two types of artifacts. The first artifact appears as a small dark spot on the output image. When an image-forming machine stops, the densitometer exposes (damages) the film in a small spot. The second artifact appears as a dark line in the output image. With continuous running, the densitometer exposes (damages) the film along a continuous line. Artifacts are not acceptable for good image quality. These artifacts usually are not permanent, taking several "refresh" cycles to clean. To avoid artifacts, emitter and collector diodes may be chosen having a longer wavelength so as not to expose the film. However, these diodes may cost significantly more than diodes currently used.

SUMMARY

This invention provides an image-forming machine with a pulse densitometer that avoids the formation of artifacts on electrophotographic films. The pulse densitometer may be used to provide pulsed emissions essentially below the exposure threshold of electrophotographic films, especially those sensitive to the infrared spectral region.

In one aspect, the image-forming machine includes a photoconductor having a film with an exposure threshold. One or more chargers, an exposure machine, a toning station, and a density measurement device are positioned adjacent to the photoconductor. The one or more chargers electrostatically charge the film. The exposure machine optically exposes and forms an electrostatic image on the film. The toning station applies toner onto the film. The toner has a charge to adhere to the electrostatic image. The density measurement device provides one or more pulses to measure the toner density, the photoconductor density, or a combination of the toner and photoconductor densities. The pulses are essentially less than the exposure threshold of the film.

In another aspect, the image-forming machine includes a photoconductor having a film with an exposure threshold. One or more chargers, an exposure machine, a toning station, and a densitometer are positioned adjacent to the photoconductor. The one or more chargers electrostatically charge the film. The exposure machine optically exposes and forms an electrostatic image on the film. The toning station applies toner onto the film. The toner has a charge to adhere to the electrostatic image. The densitometer has an emitter, a collector, and a pulse apparatus. The emitter and collector are positioned oppositely next to the photoconductor. The emitter provides one or more pulses in response to a drive signal. The one or more pulses are essentially less than the exposure threshold of the film. The one or more pulses measure the toner density, the photoconductor density, or a combination of the toner and photoconductor densities. The pulse apparatus is connected to provide the drive signal to the emitter according to a duty cycle.

In yet another aspect, an on-line densitometer for an image-forming machine has an emitter, a collector, and a pulse apparatus. The emitter provides one or more pulses according to a drive signal. The collector is positioned to receive the one or more pulses along an optical path with the emitter. The pulse apparatus connected to provide the drive signal to the emitter according to a duty cycle.

Other systems, methods, features, and advantages of the invention will be or will become apparent to one skilled in the art upon examination of the following figures and detailed description. All such additional systems, methods, features, and advantages are intended to be included within this description, within the scope of the invention, and protected by the accompanying claims.

BRIEF DESCRIPTION OF THE FIGURES

The invention may be better understood with reference to the following figures and detailed description. The components in the figures are not necessarily to scale, emphasis being placed upon illustrating the principles of the invention. Moreover, like reference numerals in the figures designate corresponding parts throughout the different views.

DETAILED DESCRIPTION OF THE PREFERRED EMBODIMENTS

Figure 1:
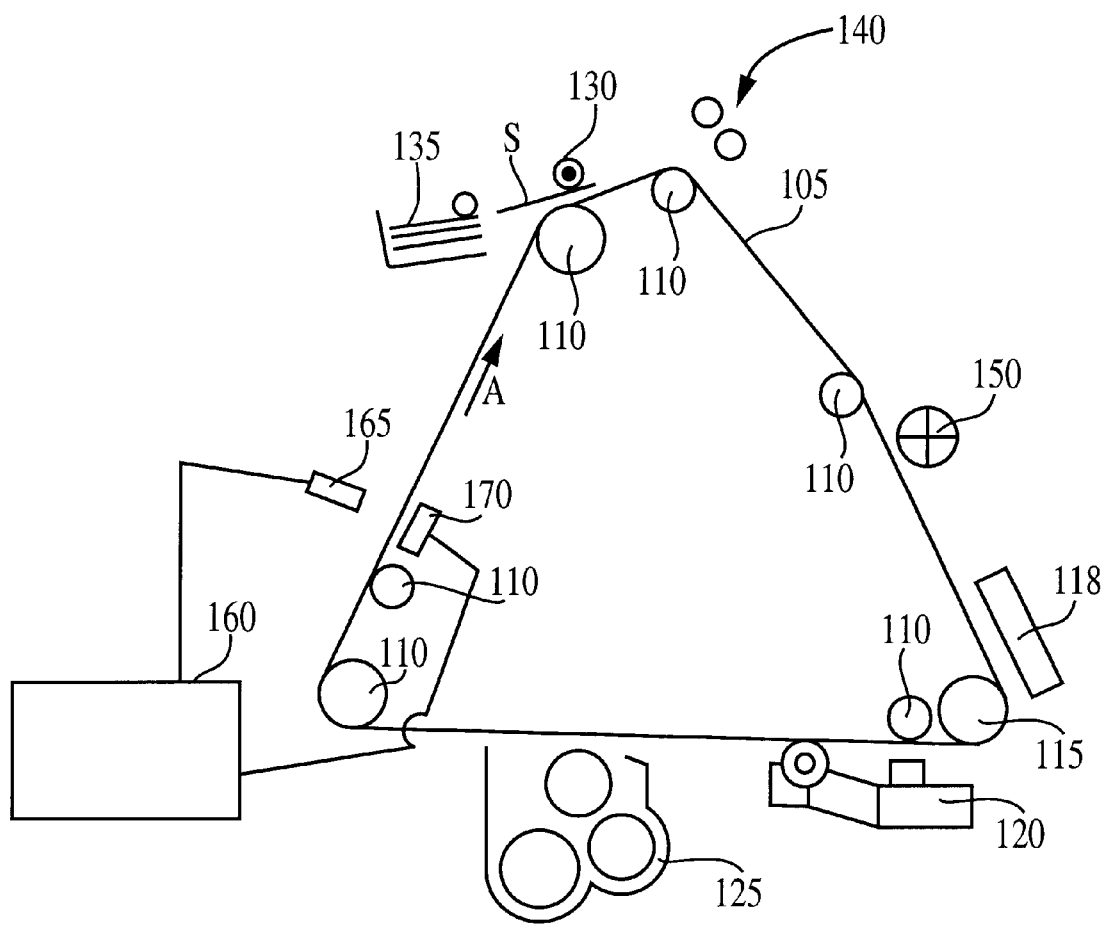
FIG. 1 represents a block diagram of an electrophotographic image-forming machine having an on-line pulse densitometer according to one embodiment.

FIG. 1 represents a block diagram of an electrophotographic (EP) image-forming machine 100 with a pulse densitometer according to one embodiment. A photoconductor 105 is operatively mounted on support rollers 110 and a motor driven roller 115, which moves the photoconductor 105 in the direction indicated by arrow A. A primary charger 118, an exposure machine 120, a toning station 125, a transfer charger 130, a fusing station 140, and a cleaner 150 are operatively disposed adjacent to the photoconductor 105. A densitometer 160 has an emitter 165 and a collector 170, which are oppositely positioned across the photoconductor 105. In one aspect, the photoconductor 105 has a belt and roller-mounted configuration. However, the photoconductor 105 may be mounted using a drum or other suitable configuration. While a particular configuration and arrangement are shown for the EP image-forming machine 100, the invention may use other configurations and arrangements including those with additional or fewer components.

Figure 2:
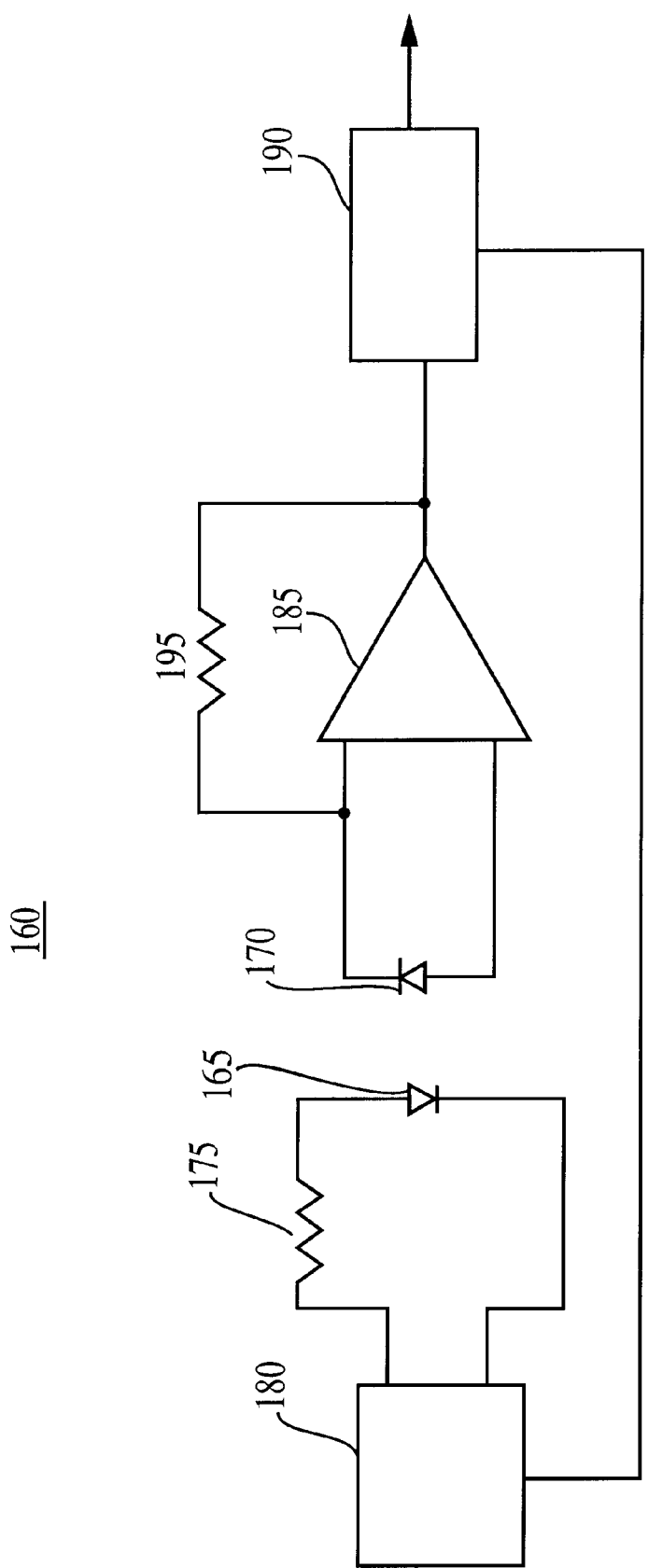
FIG. 2 represents a block diagram of an on-line densitometer according to one embodiment.

FIG. 2 represents a block diagram of the densitometer 160 according to one embodiment. The emitter 165 may be an infrared emitting diode (IRED) connected to a resistor 175 and a pulse oscillator 180. The emitter also may be a light emitting diode (LED). In one aspect, the emitter 165 is current limited by the resistor 175 and is driven by the pulse oscillator 180. The collector 170 is connected to an operational amplifier 185, which has a resistor 195 forming a feedback loop. The collector 170 may be a silicon photodiode or other photodiode. The densitometer may be a transmission densitometer, a reflection densitometer, or other density measurement device.

While a particular pulse apparatus and arrangement are described for the pulse oscillator 180, other pulse apparatus and arrangements may be used to provide the duty cycle of the densitometer for the film. The emitter 165 also may have a blocking device or shutter (not shown) that blocks and unblocks emissions from the emitter 165 in response to the duty cycle.

The emitter 165 and the collector 170 may be configured to operate with the type of film used on the photoconductor 105. By pulsing the emitter 165 below the exposure threshold of the film, the amount of emissions from the emitter 165 may not result in a significant exposure of the film even though the film may have infrared or color sensitivity. The film may be any film used in electrophotographic image-forming machines. The film may be sensitive to the wavelength of the emitter 165. The film may be sensitive to color (visible light), the infrared spectral region, and other electromagnetic emissions.

The duty cycle, wavelength, and other features of the emitter 165 and collector 170 may be selected to avoid artifacts on the film. While particular configurations are described below including particular wavelengths and duty cycles, other configurations with other wavelengths and duty cycles may be used to prevent artifacts.

The emitter 165 may have any wavelength as long as the emissions may be provided essentially below the exposure threshold of the film. In one aspect, the wavelength of the emitter 165 is selected depending upon the length of the pulses or duty cycle. In another aspect, higher wavelength emitters (not shown) are used with longer pulses or higher duty cycles. The emitter 165 may be made of GaAlAs or any other suitable material.

In this embodiment, the emitter 165 is an infrared emitting diode (IRED). The emitter 165 may have a wavelength equal to or greater than about 880 nm. In one aspect, the wavelength of the emitter is in the range of about 940 nm through about 950 nm. The emitter 165 also may have a shorter wavelength, even in the visible light range. If in the visible light range, the emitter 165 may be a light emitting diode (LED).

In this embodiment, the pulse oscillator 180 and amplifier 185 are connected to a sample-and-hold (S/H) circuit 190, which may be an integrated circuit (IC). The S/H circuit 190 may be connected to a control device (not shown) such as the logic and control unit (LCU) or other microprocessor of the EP image-forming machine 100. The S/H circuit 190 provides a voltage reading to the LCU corresponding to the density of the area read on the photoconductor 105.

In use, the emitter 165 emits pulses in response to a drive signal generated by the pulse oscillator 180. The drive signal activates and deactivates the emitter 165 according to the duty cycle. The collector or photodiode 170 is active, and may be always active, to receive incoming pulse emissions from the emitter 165. The photodiode 170 receives the pulses passing through the photoconductor 105. The amplifier 185 provides an amplified output signal to the S/H circuit 190 in response to the pulses received by the photodiode 170. The amplified output signal corresponds to the density of the photoconductor 105 and any toner. In one aspect, the density of a process patch (not shown) is measured. Other areas and densities also may be measured.

The operation of the emitter 165 may be synchronized with the operation of the S/H circuit 190. There may be time lags at the start of a pulse associated with activating the drive signal, starting the pulse emission and reception, and generating the amplified output signal. These time lags occur during a ramp-up period following the start of the drive signal or pulse. Similarly, there may be time lags at the end of a pulse associated with deactivating the drive signal, ending the pulse emission and reception, and ending generation of the amplified output signal. These time lags occur during a ramp-down period following the end of the drive signal or pulse. The presence of the amplified output signal during the ramp-up and ramp-down periods may lessen the accuracy of the density reading. To reduce or eliminate the effect of the ramp-up and ramp-down periods on the density readings, the pulse oscillator 180 provides a synchronization signal to the S/H circuit 190. The synchronization signal properly times the pulses from the emitter 165 with a hold function of the S/H circuit 190.

Figure 3:
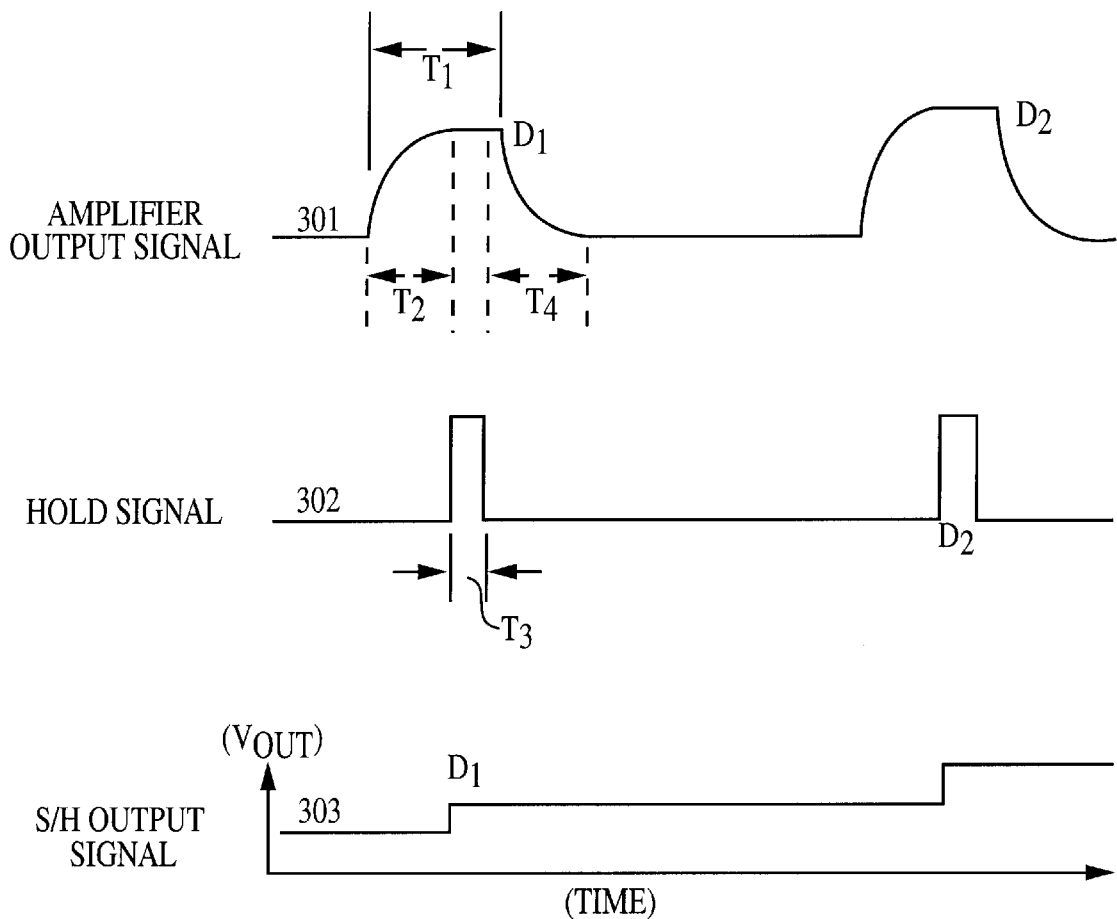
FIG. 3 represents a chart of voltage signals used by an on-line densitometer to measure density according to one embodiment.

FIG. 3 represents a chart of voltage signals used by an on-line densitometer to measure density and shows the synchronization of the emitter 165 and the S/H circuit 190 according to one embodiment. The pulse oscillator 180 generates a drive signal to measure a first density $D_1$. The drive signal causes the emitter 165 to emit a pulse during time period $T_1$. The collector or photodiode 170 receives the incoming pulse emission, thus providing an amplified output signal 301 from the amplifier 185 to the S/H circuit 190. The voltage level of the amplified output signal 301 may be a function of density. In one aspect, the amplified output signal 301 is inversely related to the density. In this aspect, a higher voltage level is less dense than a lower voltage level. In other words, as density increases (as sensed by the light received by the collector 170) the voltage level decreases.

Responsive to the synchronization signal from the pulse oscillator 180, the S/H circuit 190 takes a sample of the amplified output signal 301 during a sample period $T_3$ to obtain a hold signal 302. The sample period $T_3$ is after the ramp-up period $T_2$, but before the ramp-down period $T_4$. The hold signal 302 during sample period $T_3$ corresponds to the first density $D_1$.

The S/H circuit 190 provides an S/H output signal 303 to the LCU. The S/H circuit holds the S/H output signal 303 at the hold signal 302 taken during time period $T_3$ until the next density measurement is taken. The density measurement of the second density $D_2$ is taken in the same manner as the density measurement of the first density $D_1$. The second density $D_2$ may be lower than the first density $D_1$ (i.e., the amplified output signal 301 has a higher voltage at $D_2$ than at $D_1$). Accordingly, the S/H output signal is higher for the second density $D_2$ than the first density $D_1$. The S/H circuit 190 holds the S/H output signal 303 at this higher level until the next density measurement. While the second density $D_2$ is shown lower than the first density $D_1$, the second density $D_2$ may be higher than the first density such as when the photoconductor has the maximum amount of toner. The S/H output signal 303 may decrease and may reach about zero volts. The duty cycle also may control the timing of the density measurements for the first and second densities $D_1$ and $D_2$.

The duty cycle represents the time duration of a pulse from the emitter 165. The duty cycle may be selected depending upon the spectral response of the film on the photoconductor 105. Each film has an exposure threshold, which includes the length of time when a pulse starts to produce or produces an artifact or fogs an image on the film. In one embodiment, the duty cycle is lower than the exposure threshold of the film. In one aspect, the duty cycle is equal to or less than about five percent.

In addition, the duty cycle may be selected depending upon the "settling time" of the S/H circuit 190. The settling time is the length of time required for the S/H circuit 190 to obtain a suitable hold signal 302. The settling time includes the ramp-up time $T_2$ and the sample time $T_3$, and may also include the ramp-down time $T_4$. The ramp-up time $T_2$ may be reduced or substantially eliminated by the selection of appropriate components for the densitometer 160 such as the emitter 165, the collector 170, the amplifier 185, and others. With an appropriate selection of components, the settling time may be essentially the same as the sample time $T_3$. In addition, the sample time $T_3$ also may be reduced with the appropriate component selection. The duty cycle may be equal to or greater than the settling time. In one aspect, the duty cycle is equal to or greater than one percent.

The duty cycle may be in the range of about one percent through about five percent. When the emitter 165 is an infrared emitting diode (IRED), the temperature increase of the IRED 165 may not be significant within that range. The duty cycle may be preset by instructions in the S/H circuit 190, a microprocessor, or a control device such as the LCU. The duty cycle may be adjustable, set and changed, by the S/H circuit 190, the LCU, another microprocessor, and the like. With an adjustable duty cycle, the EP image-forming machine 100 may use different kinds of film.

Various embodiments of the invention have been described and illustrated. However, the description and illustrations are by way of example only. Many more embodiments and implementations are possible within the scope of this invention and will be apparent to those of ordinary skill in the art. Therefore, the invention is not limited to the specific details, representative embodiments, and illustrated examples in this description. Accordingly, the invention is not to be restricted except in light as necessitated by the accompanying claims and their equivalents.

What is claimed is:

1. An image-forming machine comprising:
   a photoconductor having a film with an exposure threshold;
   at least one charger operatively disposed adjacent to the photoconductor, the charger to electrostatically charge the film;
   an exposure machine operatively disposed adjacent to the photoconductor, the exposure device to optically expose and form an electrostatic image on the film;

a toning station operatively disposed adjacent to the photoconductor, the toning station to apply toner onto the film, the toner having a charge to adhere to the electrostatic image; and a density measurement device operatively disposed adjacent to the photoconductor, the density measurement device to provide at least one pulse to measure at least one of a toner density and a photoconductor density, the at least one pulse essentially less than the exposure threshold of the film.

2. An image-forming machine according to claim 1, where the density measurement device further comprises an emitter and a collector oppositely disposed adjacent to the photoconductor.

3. An image-forming machine according to claim 2, where the emitter and the collector have an optical path passing through the photoconductor.

4. An image-forming machine according to claim 2, where the emitter has a wavelength equal to or greater than about 880 nm.

5. An image-forming machine according to claim 2, where the emitter has a wavelength in the range of about 940 nm through about 950 nm.

6. An image-forming machine according to claim 2, where the emitter has a wavelength in the visible light range.

7. An image-forming machine according to claim 2, where the density measurement device further comprises a pulse apparatus connected to the emitter, the pulse apparatus to provide a drive signal to the emitter according to a duty cycle, the emitter to provide the at least one pulse in response to the drive signal.

8. An image-forming machine according to claim 7, where the pulse apparatus is a pulse oscillator.

9. An image-forming machine according to claim 7, where the density measurement device further comprises a sample-and-hold (S/H) circuit operatively connected to the pulse apparatus and the collector, the S/H circuit to receive a synchronization signal from the pulse apparatus, the S/H circuit to sample an output signal from the collector in response to the synchronization signal.

10. An image-forming machine according to claim 9, where the S/H circuit samples the output signal after a ramp-up period of the at least one pulse.

11. An image-forming machine according to claim 9, further comprising a control device, where the S/H circuit provides the output signal to the control device.

12. An image-forming machine according to claim 9, where the S/H circuit is an integrated circuit.

13. An image-forming machine according to claim 2, where the density measurement device further comprises a shutter apparatus disposed between the emitter and the photoconductor, the shutter apparatus to shield the photoconductor from the emitter according to a duty cycle.

14. An image-forming machine according to claim 2, where the emitter comprises an infrared emitting diode.

15. An image-forming machine according to claim 2, where the emitter comprises a light emitting diode.

16. An image-forming machine according to claim 2, where the collector comprises a photodiode.

17. An image-forming machine according to claim 16, where the photodiode is a silicon photodiode.

18. An image-forming machine according to claim 1, where the density measurement device has a duty cycle equal to or less than about five percent.

19. An image-forming machine according to claim 1, where the density measurement device has a duty cycle equal to or greater than about one percent.

20. An image-forming machine according to claim 1, where the film is at least one of infrared sensitive and color sensitive.

21. An image-forming machine according to claim 1, where the film further comprises a process patch, where the at least one of the toner density and the photoconductor density is of the process patch.

22. An image-forming machine comprising:

a photoconductor having a film with an exposure threshold;

at least one charger operatively disposed adjacent to the photoconductor, the charger to electrostatically charge the film;

an exposure machine operatively disposed adjacent to the photoconductor, the exposure device to optically expose and form an electrostatic image on the film;

a toning station operatively disposed adjacent to the photoconductor, the toning station to apply toner onto the film, the toner having a charge to adhere to the electrostatic image; and a densitometer having,
an emitter disposed adjacent to the photoconductor, the emitter to provide at least one pulse in response to a drive signal, the at least one pulse essentially less than the exposure threshold of the film, the at least one pulse to measure at least one of a toner density and a photoconductor density,
a collector oppositely disposed to the emitter,
a pulse apparatus connected to the emitter, the pulse apparatus to provide the drive signal to the emitter in response to a duty cycle.

23. An image-forming machine according to claim 22, where the densitometer is a transmission densitometer.

24. An image-forming machine according to claim 22, where the emitter has a wavelength greater than or equal to about 880 nm.

25. An image-forming machine according to claim 22, where the emitter has a wavelength in the range of about 940 nm through about 950 nm.

26. An image-forming machine according to claim 22, where the emitter has a wavelength in the visible light range.

27. An image-forming machine according to claim 22, where the emitter comprises an infrared emitting diode.

28. An image-forming machine according to claim 22, where the emitter comprises a light emitting diode.

29. An image-forming machine according to claim 22, where the collector comprises a photodiode.

30. An image-forming machine according to claim 22, where the duty cycle is in the range of about one percent through about five percent.

31. An image-forming machine according to claim 22, where the film is at least one of color sensitive and infrared sensitive.

32. An image-forming machine according to claim 22, where the film further comprises a process patch, where the densitometer determines the toner density on the process patch.

33. An image-forming machine according to claim 22, where the densitometer further comprises a sample-and-hold (S/H) circuit operatively connected to the pulse apparatus and the collector, the S/H circuit to receive a synchronization signal from the pulse apparatus, the S/H circuit to sample an output signal from the collector in response to the synchronization signal.

34. An image-forming machine according to claim 33, where the S/H circuit samples the output signal after a ramp-up period of the at least one pulse.

35. An on-line densitometer for an image-forming machine, comprising:
   an emitter to provide at least one pulse according to a drive signal;
   a collector disposed to receive the at least one pulse along an optical path with the emitter; and
   a pulse apparatus connected to provide the drive signal to the emitter according to a duty cycle.

36. An on-line densitometer according to claim 35, further comprising a sample-and-hold (S/H) circuit connected to the collector and the pulse apparatus, the S/H circuit to sample an output signal from the collector in response to a synchronization signal from the pulse apparatus.

37. An on-line densitometer according to claim 36, where the S/H circuit samples the output signal after a ramp-up period of the at least one pulse.

38. An on-line densitometer according to claim 36, where the S/H circuit is an integrated circuit.

39. An on-line densitometer according to claim 36, further comprising an amplifier operatively connected to the collector and the S/H circuit, where the amplifier provides the output signal from the collector to the S/H circuit.

40. An on-line densitometer according to claim 39, where the amplifier is an operational amplifier.

41. An on-line densitometer according to claim 35, where the emitter has a wavelength equal to or greater than about 880 nm.

42. An on-line densitometer according to claim 35, where the emitter has a wavelength in the range of about 940 nm through about 950 nm.

43. An on-line densitometer according to claim 35, where the emitter has a wavelength in the visible light range.

44. An on-line densitometer according to claim 35, where the emitter comprises an infrared emitting diode.

45. An on-line densitometer according to claim 35, where the emitter comprises a light emitting diode.

46. An on-line densitometer according to claim 35, where the collector comprises a photodiode.

47. An on-line densitometer according to claim 46, where the photodiode is a silicon photodiode.

48. An on-line densitometer according to claim 35, where the duty cycle is less than an exposure limit of a film for a photoconductor.

49. An on-line densitometer according to claim 35, where the duty cycle is in the range of about one percent through about five percent.

* * * * *

UNITED STATES PATENT AND TRADEMARK OFFICE
CERTIFICATE OF CORRECTION

PATENT NO.   : 6,427,057 B1
DATED        : July 30, 2002
INVENTOR(S)  : Hameister et al.

It is certified that error appears in the above-identified patent and that said Letters Patent is hereby corrected as shown below:

Title page,
Insert Item -- [60], Related U.S. Application Data,
        This application is based on Provisional Application No. 60/225,486 filed on 8/15/2000 --

Signed and Sealed this

Twenty-second Day of March, 2005

JON W. DUDAS
*Director of the United States Patent and Trademark Office*